United States Patent [19]

Dolle et al.

[11] Patent Number: 5,462,939
[45] Date of Patent: Oct. 31, 1995

[54] PEPTIDIC KETONES AS INTERLEUKIN-1β-CONVERTING ENZYME INHIBITORS

[75] Inventors: Roland E. Dolle, King of Prussia; Todd L. Graybill, Pottstown; Gary J. Speier, WestChester; Catherine P. Prouty, Wayne; Stanley J. Schmidt, Chester Springs, all of Pa.

[73] Assignee: Sterling Winthrop Inc., New York, N.Y.

[21] Appl. No.: 60,197

[22] Filed: May 7, 1993

[51] Int. Cl.⁶ .................. A61K 31/535; A61K 37/00; C07D 409/00
[52] U.S. Cl. .................. 514/231.5; 514/311; 514/314; 514/307; 514/336; 514/357; 514/18; 514/19; 514/444; 514/471; 514/399; 514/365; 514/438; 514/397; 549/29; 549/60; 549/318; 544/152; 548/204; 548/315.4; 546/147; 546/164; 546/268; 546/329; 530/330; 530/331
[58] Field of Search .................. 514/471, 231.5, 514/18, 19, 444, 311, 314, 307, 336, 357, 399, 397, 365, 438; 549/318, 60, 29; 544/152, 204; 530/330, 331; 546/147, 164, 268, 329; 548/315.4

[56] References Cited

U.S. PATENT DOCUMENTS

| | | | |
|---|---|---|---|
| 4,965,283 | 10/1990 | Klessing et al. | 549/318 |
| 5,055,451 | 10/1991 | Krantz et al. | 514/19 |

FOREIGN PATENT DOCUMENTS

| | | |
|---|---|---|
| 0519748A2 | 6/1992 | European Pat. Off. . |
| WO91/15577 | 10/1991 | WIPO . |

*Primary Examiner*—C. Warren Ivy
*Assistant Examiner*—Amelia Owens
*Attorney, Agent, or Firm*—Imre (Jim) Balogh; William J. Davis; Paul E. Dupont

[57] ABSTRACT

Disclosed are compounds of the formula (I) and pharmaceutically acceptable salts thereof:

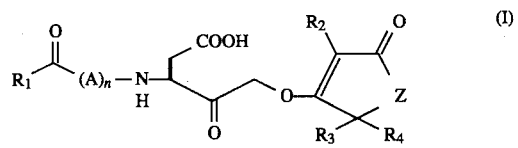

wherein $R_1$ is $(CR_5R_6)_n$, $(CR_5R_6)_n$-aryl, $(CR_5R_6)_n$-heteroaryl, $X-(CR_5R_6)_n$, $X-(CR_5R_6)_n$-aryl or $X-(CR_5R_6)_n$-heteroaryl wherein aryl and heteroaryl may be optionally substituted;

X is O or $NR_5$;

$R_5$ and $R_6$ are independently H or lower alkyl;

$R_2$ is H, halo, lower alkyl or $(CR_5R_6)_n$-aryl;

$R_3$ and $R_4$ are independently H or alkyl;

A is a D or L isomer of an amino acid selected from the group consisting of alanine, valine, leucine, isoleucine, proline, phenylalanine, glycine, tyrosine, methionine, asparagine, glutamine, aspattic acid, glutamic acid, lysine, arginine, histidine and β-thienylalanine;

Z is $CH_2$ or O; and n is 0–4;

pharmaceutical compositions containing the compounds; and a method for inhibiting interleukin-1β protease activity in a mammal utilizing the compounds and compositions.

15 Claims, No Drawings

PEPTIDIC KETONES AS INTERLEUKIN-1β-CONVERTING ENZYME INHIBITORS

BACKGROUND OF THE INVENTION

1. Field of the Invention

This invention relates to a series of novel amino acid analogs which exhibit selective inhibition of interleukin-1β-converting enzyme, to compositions containing the novel amino acid analogs and methods for therapeutic utility. More particularly, the interleukin-1β-converting enzyme inhibitors described in this invention comprise novel amino acid methyl ketones which possess particular utility in the treatment of inflammatory, immune-based diseases and cancer.

2. Reported Developments

Interleukin-1β protease (also known as interleukin-1β-converting enzyme or ICE) is the enzyme responsible for processing of the biologically inactive 31 kD precursor IL-1β to the biologically active 17 kD form (Kostura, M. J.; Tocci, M. J.; Limjuco, G.; Chin, J.; Cameron, P.; Hillman, A. G.; Chartrain, N. A.; Schmidt, J. A. *Proc. Nat. Acad. Sci.*, 1989, 86, 5227–5231 and Black, R. A.; Kronheim, S. R.; Sleath, P. R. *FEBS Let.*, 1989, 247, 386–391). In addition to acting as one of the body's early responses to injury and infection, IL-1β has also been proposed to act as a mediator of a wide variety of diseases, including rheumatoid arthritis, osteoarthritis, inflammatory bowel disease, sepsis, and acute and chronic myelogenous leukemia (Dinarello, C. A.; Wolff, S. M., *New Engl. J. Med.*, 1993, 328, 106). The naturally occurring IL-1β receptor antagonist has been used to demonstrate the intermediacy of IL-1β in a number of human diseases and animal models (Hannum, C. H.; Wilcox, C. J.; Arend, W. P.; Joslin, G. G.; Dripps, D. J.; Heimdal, P. L.; Armes, L. G.; Sommer, A.; Eisenberg, S. P.; Thompson, R. C., *Nature*, 1990, 343, 336–340; Eisenberg, S. P.; Evans, R. J.; Arend, W. P.; Verderber, E.; Brewer, M. T.; Hannum, C. H.; Thompson, R. C., *Nature* 1990, 343, 341–346; Ohlsson, K.; Bjork, P.; Bergenfeldt, M.; Hageman, R.; Thompson, R. C., *Nature*, 1990, 348, 550–552; and Wakabayashi, G., *GASEB*, 1991, 338–343). The specific role of IL-1β in inflammation and immunomodulation is supported by the recent observation that the cowpox virus employs an inhibitor of ICE to suppress the inflammatory response of its host (Ray, C. A. et al, *Cell*, 1992, 69, 597–604).

The present invention also relates to the modulation of processing of IL-1β for the treatment of rheumatoid arthritis. Levels of IL-1β are known to be elevated in the synovial fluid of patients with the disease. Additionally, IL-1β stimulates the synthesis of enzymes believed to be involved in inflammation, such as collagenase and PLA2, and produces joint destruction which is very similar to rheumatoid arthritis following intraarticular injection in animals.

A limited number of peptidyl methyl ketone analogs constitute a well-known class of compounds having cysteine protease (papain, cathepsin B) inhibitory activity. These peptidyl methyl ketone analogs have been reviewed by D. Rich in Chapter 4 of "Proteinase Inhibitors", Barrett, A. J. and Salvensen, G., eds., Elsevier, 1986. More recently, α-aryloxy and α-arylacyloxy methyl ketones have also been described as inhibitors of cysteine protease (Krantz, A. et al, Biochemistry, 30, p. 4678–4687, 1991).

These peptide analogs, however, are essentially devoid of potency and selectivity in inhibiting ICE.

An effective therapy has yet to be developed for the treatment of IL-1β mediated inflammatory diseases. Consequently, there is a need for therapeutic agents effective in the treatment and prevention of these diseases.

SUMMARY OF THE INVENTION

In accordance with the present invention, novel peptidic ketones are provided having the formula (I) and a pharmaceutically acceptable salt thereof

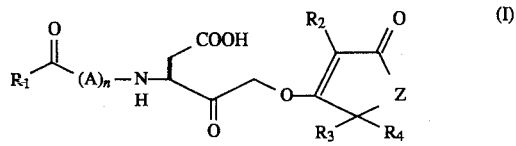

wherein $R_1$ is $(CR_5R_6)_n$, $(CR_5R_6)_n$-aryl, $(CR_5R_6)_n$-heteroaryl, $X\text{-}(CR_5R_6)_n$, $X(CR_5R_6)_n$-aryl or $X\text{-}(CR_5R_6)_n$-heteroaryl wherein aryl and heteroaryl may be optionally substituted;

X is O or $NR_5$;

$R_5$ and $R_6$ are independently H or lower alkyl;

$R_2$ is H, halo, lower alkyl or $(CR_5R_6)_n$-aryl;

$R_3$ and $R_4$ are independently H or alkyl;

A is a D or L isomer of an amino acid selected from the group consisting of alanine, valine, leucine, isoleucine, proline, phenylalanine, glycine, tyrosine, methionine, asparagine, glutamine, aspartic acid, glutamic acid, lysine, arginine, histidine and β-thienylalanine;

Z is $CH_2$ or O; and n is 0–4.

As used herein, the term amino acid includes both D and L isomers thereof and the pharmaceutically acceptable salts include the acid and base addition salts.

The term acid addition salts refers to those salts which retain the biological effectiveness and properties of the free bases and which are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

The term base addition salts include those derived from inorganic bases such as sodium, potassium, lithium, ammonium, calcium, magnesium, iron, zinc, copper, manganese, aluminum salts and the like. Particularly preferred are the ammonium, potassium, sodium, calcium and magnesium salts derived from pharmaceutically acceptable organic nontoxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, trimethamine, dicyclohexylamine, lysine, arginine, histidine, caffeine, procaines, hydrabamine, choline, betaine, ethylenediamine, glucosamine, methylglucamine, theobromine, purines, piperazine, piperidine, N-ethylpiperidine, polyamine resins and the like. Particularly preferred organic non-toxic bases are isopropylamine, diethylamine, ethanolamine, trimethamine, dicyclohexylamine, choline and caffeine.

"Alkyl" is defined as a saturated or unsaturated aliphatic hydrocarbon which may be either straight- or branched-chain. Preferred groups have no more than about 12 carbon atoms and may be methyl, ethyl and structural isomers of propyl, butyl, pentyl, hexyl, heptyl, octyl, nonyl, decyl, undecyl and dodecyl.

"Lower alkyl" is defined as an alkyl group as above, having 1 to 4 carbon atoms. Suitable lower alkyl groups are methyl, ethyl, n-propyl, isopropyl, butyl, tert-butyl, n-pentyl, neopentyl, n-hexyl, and n-heptyl.

"Aryl" is defined as phenyl, naphthyl and substituted phenyl.

"Substituted phenyl" is defined as a phenyl group in which one or more of the hydrogens has been replaced by the the same or different substituents including halo, lower alkyl, nitro, amino, acylamino, hydroxyl, lower alkoxy, aryl, heteroaryl, lower alkoxy, alkyl sulfonyl, trifluoromethyl, morpholinoethoxy and morpholino-sulfonyl, and carbobenzoxy-methyl sulfamoyl.

"Halogen" is defined as chloride, fluoride, bromide or iodide.

"Heteroaryl" is defined as pyridyl, thienyl, furyl, thiazolyl, imidazolyl, pyrazolyl, triazinyl, quinolyl and isoquinolyl.

"Substituted heteroaryl" means a heteroaryl group in which one or more of the hydrogens has been replaced by the the same or different substituents including halo, lower alkyl, nitro, amino, acylamino, hydroxyl, lower alkoxy, aryl, heteroaryl, lower alkoxy, alkylsulfonyl, trifluoromethyl, morpholinoethoxy, morpholino-sulfonyl, carbobenzoxymethylsulfamoyl.

The present invention concerns a method for inhibiting ICE in a mammal by administering a therapeutically effective amount of a compound of the Formula (I) or a pharmaceutical composition containing a compound of the Formula (I) in a pharmaceutically acceptable carrier. The method of inhibition is directed for the treatment of IL-1β mediated disease states or disorders which include: infectious diseases, such as meningitis and salpingitis; septic shock, respiratory diseases; inflammatory conditions, such as arthritis, cholangitis, colitis, encephalitis, endocerolitis, hepatitis, pancreatitis and reperfusion injury, immune-based diseases, such as hypersensitivity; auto-immune diseases, such as multiple sclerosis; bone diseases; and certain tumors.

The pharmaceutical composition of the present invention comprises an active ingredient of the compound of formula (I) in admixture with a pharmaceutically acceptable, non-toxic carrier. Such compositions may be prepared for use for parenteral (subcutaneous, intraarticular, intramuscular or intravenous) administration, particularly in the form of liquid solutions or suspensions; for oral or buccal administration, particularly in the form of tablets or capsules; or intranasally, particularly in the form of powders, nasal drops or aerosols.

When administered orally (or rectally) the compounds will usually be formulated into a unit dosage form such as a tablet, capsule, suppository or cachet. Such formulations typically include a solid, semi-solid or liquid carrier or diluent. Exemplary diluents and vehicles are lactose, dextrose, sucrose, sorbitol, mannitol, starches, gum acacia, calcium phosphate, mineral oil, cocoa butter, oil of theobroma, alginates, tragacanth, gelatin, syrup, methylcellulose, polyoxyethylene sorbitan monolaurate, methyl hydroxybenzoate, propyl hydroxybenzoate, talc, and magnesium stearate.

The compositions may be prepared by any of the methods well-known in the pharmaceutical art, for example as described in *Remington's Pharmaceutical Sciences*, 17th edition, Mack Publishing Company, Easton, Penna., 1985. Formulations for parenteral administration may contain as common excipients sterile water or saline, alkylene glycols such as propylene glycol, polyalkylene glycols such as polyethylene glycol, oils of vegetable origin, hydrogenated naphthalenes and the like. Examples of vehicles for parenteral administration include water, aqueous vehicles such as saline, Ringer's solution, dextrose solution, and Hank's solution and nonaqueous vehicles such as fixed oils (such as corn, cottonseed, peanut, and sesame), ethyl oleate, and isopropyl myristate. Sterile saline is a preferred vehicle and the compounds are sufficiently water soluble to be made up as a solution for all foreseeable needs. The vehicle may contain minor amounts of additives such as substances that enhance solubility, isotonicity, and chemical stability, e.g., antioxidants, buffers, and preservatives. For oral administration, the formula can be enhanced by the addition of bile salts and also by the addition acylcarnitines (*Am. J, Physiol.* 251:3332 (1986). Formulations for nasal administration may be solid and contain as excipients, for example, lactose or dextran, or may be aqueous or oily solutions for administration in the form of nasal drops or metered spray. For buccal administration typical excipients include sugars, calcium stearate, magnesium stearate, pregelatinated starch, and the like.

When formulated for nasal administration the absorption across the nasal mucous membrane is enhanced by surfactant acids, such as for example, glycocholic acid, cholic acid, taurocholic acid, ethocholic acid, desoxycholic acid, chenodesoxycholic acid, dehydrocholic acid, glycodeoxycholic acid, and the like (See, B. H. Vickery, "LHRH and its Analogs-Contraception and Therapeutic Applications", Pt.2, B. H. Vickery and J. S. Nester, Eds., MTP Press, Lancaster, UK, 1987).

In general, for the uses as described in the present invention, it is expedient to administer the active ingredient in amounts between about 0.1 and 100 mg/kg body weight, most preferably from about 0.1 to 30 mg/kg body weight for human therapy, the active ingredient will be administered preferably in the range of from about 0.1 to about 20–50 mg/kg/day. This administration may be accomplished by a single administration, by distribution over several applications or by slow release in order to achieve the most effective results. When administered as a single dose, administration will most preferably be in the range of from about 0.1 to 10 mg/kg of body weight.

The exact dose and regimen for administration of these compounds and compositions will necessarily be dependent upon the needs of the individual subject being treated, the type of treatment, and the degree of affliction or need. In general, parenteral administration requires lower dosage than other methods of administration which are more dependent upon absorption.

DETAILED DESCRIPTION OF THE INVENTION

Compounds of the present invention are prepared according to Schemes I and III.

Scheme I

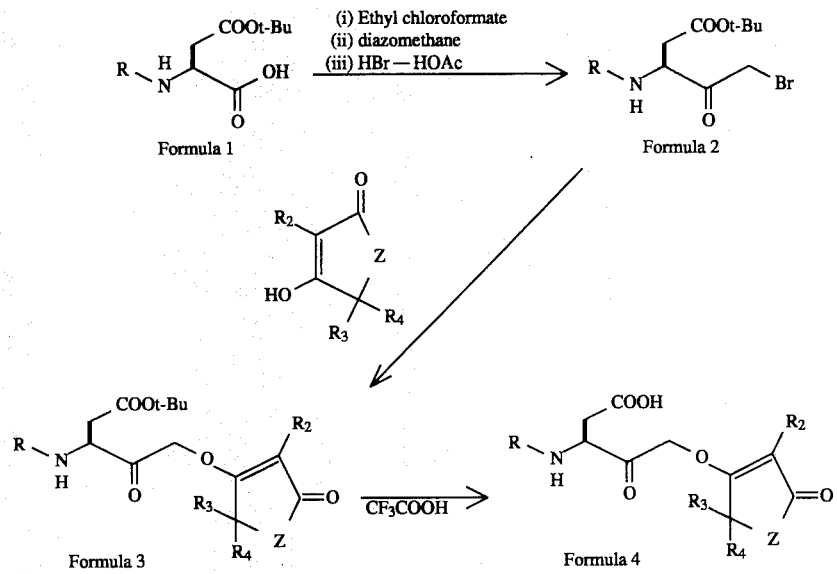

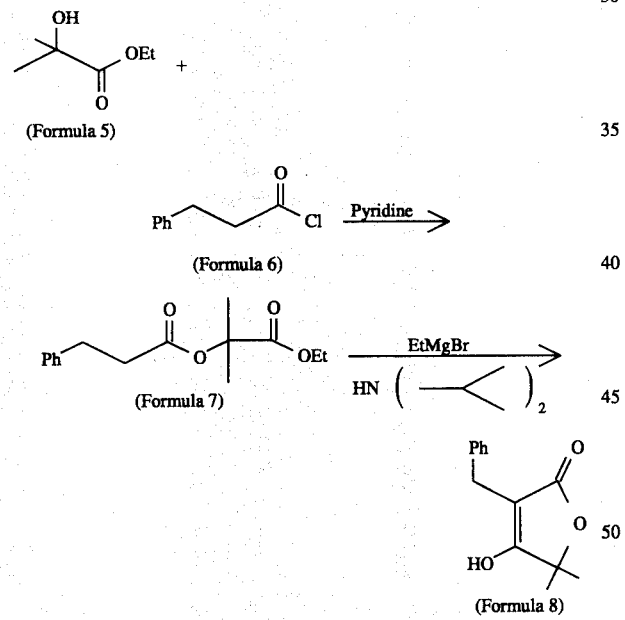

wherein $R_2$, $R_3$, $R_4$ and Z are as defined in formula (I) above, and R is $R_1CO(A)_n$ wherein $R_1$, A and n are as defined in formula (I) above.

The first step of this procedure involves the synthesis of N-protected amino acid bromomethyl ketone (Formula 2). Methods for the preparation of various amino acids and peptides (Formula 1) are well established in the art. The N-protected amino acids, dipeptides, and polypeptides which in some cases are commercially available or prepared by standard methodology as described in *The Practice of Peptide Synthesis*, M. Bodansky, Springer-Verlag, N.Y. 1984, are then converted to the aspartic acid bromomethyl ketone (Formula 2) by way of acid-catalyzed decomposition of a diazomethyl ketone intermediate (Krantz, A. et al, *Biochemistry*, 1991, 30, 4678–4687).

The N-protected amino acid bromomethyl ketone (Formula 2) is reacted with a variety of tetronic acids or cyclopentadiones. This is conducted by exposing the bromomethyl ketone to an excess of the tetronic or cyclopentadione in DMF containing sodium or potassium hydride or potassium fluoride. The reaction can be conveniently monitored by thin layer chromatography (TLC) and once the TLC indicates that the displacement of the bromide with the tetronic acid or cyclopentadione is completed, the product is isolated using standard procedures. The desired aspartic acid-based mono-t-butyl ester tetronoyloxymethyl or cyclopentadionoyloxy methyl ketone (Formula 3) may be purified by conventional methods including recrystallization and silica gel column chromatography.

The tetronic acids and the cyclopentadiones used in the reaction with the bromomethyl ketones can be either purchased from commercial sources or synthesized by adopting known procedures (Haynes, L. J., J. Chem. Soc., PArt I, 1956, 4103–4106; White, J. D. et al, J. Amer. Chem. Soc. 1982, 104, 3923; Ramage, R. et al, *J. Chem. Soc. Perkin Trans, I*, 1984, 1539– 1545; Martinez, R. A. et al,. *Syn. Commun.*, 1989, 19, 373–377; Pandey, B. et al, *Syn, Commun,* 1989, 19, 2741–2747). Their synthesis would be readily deduced by those skilled in the art of organic synthesis. By way of example, the preparation of the 3-benzyl-5,5-dimethyl (Formula 8) is presented in Scheme II.

The following examples further illustrate the invention and are not to be construed as limiting of the specification and claims in any way.

EXAMPLE 1

N-Benzyloxycarbonyl-L-aspartic acid 2-phenyltetronoyloxymethyl ketone

A reaction mixture was prepared containing N-benzyloxycarbonyl-L-aspartic acid bromomethyl ketone β-tert-butyl ester (0.63 mmol, 0.25 g) 1.2 equiv. of phenyl tetronic acid (0.75 mmol, 0.13 g) and 2.5 equiv. of KF (1.57 mmol, 0.09 g) in a solution of anhydrous DMF (7 mL). The reaction mixture was stirred overnight at 25° C. The reaction mixture was diluted with ethyl acetate and washed with water, saturated aqueous NaHCO$_3$, brine and dried over Na$_2$SO$_4$. The extract was filtered and the solvent was removed in vacuo to yield a crude product as an oil. The oil was dissolved in 2 mL of ethyl acetate and hexane was added until a slightly turbid solution was obtained which was then cooled at 4° C. for 12 hrs. Analytically pure N-benzyloxycarbonyl-L-aspartic acid 2-phenyltetronoyloxymethyl ketone β-tert-butyl ester was obtained as a white solid (0.2 g, 69%): mp 85–87° C. $^1$H NMR (300 MHz, CDCl$_3$) δ:7.82 (d, J=7.57 Hz, 2H), 7.41–7.36 (m, 8H), 7.60 (d, J=8.0 Hz, 2H), 5.12–5.08 (m, 4H), 4.71–4.66 (m, 2H), 4.48–4.37 (ddd, J=8.0, 5.1, 4.4 Hz, 1H), 3.08–3.00 (dd, J=17.7, 4.4 Hz, 1H), 2.73–2.67 (dd, J=17.7, 5.1 Hz, 1H), 1.43 (s, 9H).

The tert-butyl ester (0.34 mmol, 0.17 g) was dissolved in 25% trifluoroacetic acid-methylene chloride (v/v, 15 mL) and toluene (2 mL). The reaction was stirred at 25° C. and judged complete (TLC) within 1 hr. The solvents were removed in vacuo and the residue was azeotroped several times with methylene chloride. N-benzyloxycarbonyl-L-aspartic acid 2-phenyltetronoyloxymethyl ketone was obtained as a pure white solid (0.123 g, 82%) mp 64–67° C. $^1$H NMR (300 MHz, DMSO) δ:7.98 (d, J=7.6 Hz, 2H), 7.87 (d, J=7.15 Hz, 2H), 7.43–7.27 (m, 8H), 5.34 (s, 2H), 5.11 (s, 2H), 4.90 (m, 2H), 5.58–4.87 (ddd, J=7.6, 7.1, 5.8 Hz, 1H), 2.84–2.77 (dd, J=16.9, 5.8 Hz, 1H), 2.67–2.58 (dd, 17.0, 7.1 Hz, 1H).

C, H, N calculated for C$_{23}$H$_{21}$NO$_8$. 0.25 H$_2$O. calc: % C=62.23, % H=4.88, % N=3.16. found: % C=62.20, % H=4.89, % N=3.07.

Utilizing appropriate starting materials and reagents, and following the procedures described in Schemes I and II and Example 1, the following compounds were prepared.

EXAMPLE 2

N-Benzyloxycarbonyl-L-aspartic acid 2-(3,4-dichlorophenyl) tetronoyloxymethyl ketone C, H, N calculated for C$_{23}$H$_{19}$Cl$_2$NO$_8$. calc: % C=54.35, % H=3.77, % N=2.76. found: % C=54.30, % H=3.80, % N=2.67.

EXAMPLE 3

N-Benzyloxycarbonyl-L-aspartic acid 2-benzyl-5,5-dimethyl tetronoyloxymethyl ketone C, H, N calculated for C$_{26}$H$_{27}$NO$_8$. 0.5 H$_2$O. calc: % C=63.67, % H=5.75, % N=2.86. found: % C=63.93, % H=5.70, % N=2.88.

EXAMPLE 4

N-Benzyloxycarbonyl-L-aspartic acid tetronoyloxymethyl ketone

C, H, N calculated for C$_{17}$H$_{17}$NO$_8$. calc: % C=56.20, % H=4.72, % N=3.86. found: % C=55.83, % H=4.63, % N=3.80.

EXAMPLE 5

N-Benzyloxycarbonyl-L-aspartic acid 2-(4-methoxyphenyl) tetronoyloxymethyl ketone FAB MS spectra: m/z=470 [M+H]$^+$. $^1$H NMR (300 MHz, DMSO) δ:7.82 (d, J=8.9 I-tz, 2H), 7.38–7.34 (m, 5H), 6.97 (d, J=8.9 Hz, 2H), 5.3 (s, 2H), 5.07 (s, 2H), 4.88–4.86 (m, 2H), 4.53–4.51 (m, 1H), 3.75 (s, 3H), 2.84–2.77 (dd, J=17.0, 5.7 Hz, 1H), 2.66–2.58 (dd, J=17.0, 7.0 Hz, 1H).

EXAMPLE 6

N-Benzyloxycarbonyl-L-aspartic acid 2-benzyl tetronoyloxymethyl ketone $^1$H NMR (300 MHz, DMSO) 5:7.96 (d, J=7.4 Hz, 1H), 7.4–7.1 (m, 10H), 5.2 (s, 2H), 5.06 (s, 2H), 4.77 (m, 2H), 4.50 (m, 1H), 3.44 (s, 1H), 2.80 (dd, J=17.0, 5.7 Hz, 1H), 2.62 (dd, J=17.0, 7.0 Hz, 1H).

EXAMPLE 7

N-Benzyloxycarbonyl-L-valine-L-aspartic acid 2-phenyl tetronoyloxymethyl ketone $^1$H NMR (300 MHz, DMSO) δ:8.85 (d, J=6.5 Hz, 1H), 7.86 (d, J=7.6 Hz, 2H), 7.53 (d, J=6.6 Hz, 1H), 7.43–7.33 (m, 8H), 5.24 (s, 2H), 5.02 (s, 2H), 4.84–4.71 (m, 2H), 4.58–4.51 (m, 1H), 3.85–3.80 (m, 1H), 2.88–2.81 (dd, J=17.0, 4.4 Hz, 1H), 2.62–2.54 (dd, J=17.3, 8.0 Hz, 1H), 1.97–1.90 (m, 1H) 0.86 (d, J=6.9 Hz, 6H).

EXAMPLE 8

N-Benzyloxycarbonyl-L-aspartic acid 2-phenyl-5,5-dimethyl tetronoyloxymethyl ketone Low resolution mass spectrum m/z 468 (M+H).

EXAMPLE 9

N-Benzyloxycarbonyl-L-valine-L-aspartic acid 2-benzyl tetronoyloxymethyl ketone

Low resolution mass spectrum m/z 553 (M+H), 509, 273.

EXAMPLE 10

N-Benzyloxycarbonyl-L-aspartic acid 4,4-dimethyl tetronoyloxymethyl ketone

C,H,N calculated for C$_{19}$H$_{21}$NO$_8$0.8 H$_2$O: calc: % C=56.23, % H=5.61, % N=3.45. found % C=56.22, % H=5.37, % N=3.42.

EXAMPLE 11

N-Benzyloxycarbonyl-L-aspartic acid 2-chloro tetronoyloxymethyl ketone

C,H,N calculated for C$_{17}$H$_{16}$ClNO$_8$: calc: % C=51.33, % H=4.05, % N=3.52. found: % C=51.05, % H=4.05, % N=3.40.

EXAMPLE 12

N-Benzyloxycarbonyl-L-valine-L-alanine-L-aspartic acid 2-benzyl tetronoyloxymethyl ketone $^1$H NMR (300 MHz, DMSO) 0.82 (d, 3H), 0.90 (D, 3H), 1.20 (d, 3H), 2.55 (dd, 1H), 2.80 (dd, 1H), 3.15 (d, 1H), 3.30 (d, 1H), 3.80 (m, 1H), 4.15 (m, 1H), 4.40 (m, 1H), 4.60 (d, 1H), 4.70 (d, 1H), 5.0 (m, 2H), 5.15 (dd, 1H), 5.25 (dd, 1H), 7.25 (m, 10H), 8.20 (d, 1H), 8.85 (d, 1H).

EXAMPLE 13

N-Benzyloxycarbonyl-L-aspartic acid 2-methyl cyclopentadionoyloxy methyl ketone C,H,N calculated for $C_{19}H_{21}NO_7$: calc: % C=60.79, % H=5.64, % N=3.73. found: % C=60.59, % H=5.64, % N=3.50.

EXAMPLE 14

N-Benzyloxycarbonyl-L-aspartic acid 2-phenylcyclopentadionoyloxymethyl ketone FAB MS spectra: m/z=438 [M+H]$^+$. $^1$H NMR (300 MHz, DMSO) δ:7.99 (d, J=7.6 Hz, 1H), 7.72 (d, J=7.2 Hz, 2H),7.37–7.34 (m, 8H), 5.35 (s, 2H), 5.07 (s, 2H), 4.52–4.50 (m, 1H), 2.83–2.77 (dd, J=17.0, 6.1 Hz, 1H), 2.63–2.58 (m, 4H), 2.49–2.43 (m, 2H).

The tetronic acid used in the preparation of Example 3 is presented in Example 15:

EXAMPLE 15

3-Benzyl-5,5-dimethyltetronic acid (Formula 8, Scheme II)

Ethyl 2-hydroxy isobutyrate (39.6 g, 0.30 mol) (Formula 5, Scheme II) and pyridine (80 mL) were stirred together and cooled to 0° C. Hydrocinnamoyl chloride (Formula 6, Scheme II) (67.4 g, 0.40 mol) was added dropwise with cooling and mechanized stirring. The resulting heterogeneous mixture was stirred for 5 hrs. The mixture was poured into water. Addition of 10% $H_2SO_4$ helped break up the resulting emulsion. The aqueous layer was extracted with ether. The organic layer was then washed with 10% $H_2SO_4$ and sat. $NaHCO_3$, dried over $Na_2SO_4$ and concentrated. The diester (Formula 7, Scheme II) was then obtained as a colorless oil (26.8 g, 34%) by distillation (112–115° C., 0.1 mm Hg).

Diisopropylamine (30.3 g, 0.30 mol) in 50 mL of ether was added to an ice-cold solution of ethyl magnesium bromide (2.0 M solution in TMF, 150 mL, 0.30 mol). The reaction was then stirred at room temperature for 20 min. The solution was re-cooled to 0° C. and a solution of diester, obtained above (26.8 g, 0.1 mol) was added for 20 min. Upon warming to 40° C., the reaction became homogeneous. After 20 min. of stirring, the reaction solution was poured over ice and concentrated HCl. The acidified aqueous layer was extracted with ether. The ether phase was then washed with 5% HCl (2×) and extracted with 5% $K_2CO_3$ solution (4×). The basic aqueous phase was then washed with ether (2×) and acidified by addition of dilute HCl. The oil which separated was redissolved in ether. Evaporation of the ether produced a yellow oil which slowly solidified after scratching. The title compound, (Formula 8, Scheme II) was obtained.

Compounds of the present invention were tested for IL-1β protease inhibition activity according to the following protocol: Partially purified IL-1β protease is stored at −80° C., thawed on ice, and preincubated for 10 minutes at 37° C. with 2.5 mM dithiothreitol in a buffer solution containing 10 mM Tris-HCl (pH 8.0) and 25% (v/v) glycerol. Inhibitors are prepared as stock solutions in dimethyl sulfoxide (DMSO). The protease is preincubated with inhibitor in a volume of 20 μL in a 1.5 mL polypropylene microcentrifuge tube for 15 minutes at 37° C. The volume of compound added to the assay is adjusted to yield a DMSO concentration in the preincubation of <15% (v/v). The enzyme assay is then initiated by the addition of substrate (TRITC-AYVH-DAPVRS-$NH_2$) to yield a final concentration of 67 μM in a final volume of 30 μL. The reactions are carried out for 60 minutes at 37° C. in the dark and are terminated by the addition of 10 μL of 10% trifluoroacetic acid (TFA). Following the addition of 115 μL of 0.1% TFA, the samples are analyzed by high pressure liquid chromatography using a reverse phase (C18) column and elution with an acetonitrile/water/TFA gradient. Substrate and product are monitored by their absorbance at 550 nm and elute at 4.2 and 5.2 minutes, respectively.

The compounds tested were found to have IL-Iβ protease inhibitory activity of $IC_{50}$<10 μM.

Although the invention has been described in the context of particular embodiments, it is intended that the scope of coverage of the patent not be limited to those particular embodiments, but be determined by reference to the following claims.

What is claimed is:

1. A compound of the formula (I) or a pharmaceutically acceptable salt thereof:

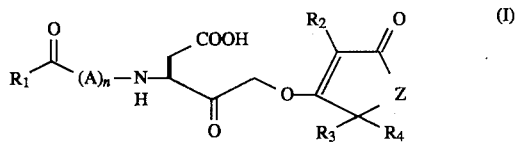

wherein $R_1$ is $(CR_5R_6)_n$, $(CR_5R_6)_n$-aryl, $(CR_5R_6)_n$-heteroaryl, X-$(CR_5R_6)_n$, X-(CR $_5R_6)_n$-aryl or X-$(CR_5R_6)_n$-heteroaryl wherein aryl and heteroaryl may be optionally substituted;

X is O or $NR_5$;

$R_5$ and $R_6$ are independently H or lower alkyl;

$R_2$ is H, halo, lower alkyl or $(CR_5R_6)_n$-aryl;

$R_3$ and $R_4$ are independently H or alkyl;

A is a D or L isomer of an amino acid selected from the group consisting of alanine, valine, leucine, isoleucine, proline, phenylalanine, glycine, tyrosine, methionine, asparagine, glutamine, aspartic acid, glutamic acid, lysine, arginine, histidine and β-thienylalanine;

Z is $CH_2$ or O; and n is 0–4.

2. The compound of claim 1 wherein said aryl is phenyl, naphthyl or substituted phenyl.

3. The compound of claim 2 wherein said phenyl is substituted by halo, lower alkyl, nitro, amino, acylamino, hydroxyl, lower alkoxy, trifluoromethyl, alkyl sulfonyl, morpholinoethoxy or morpholinosulfonyl.

4. The compound of claim 1 wherein said heteroaryl is pyridyl, thienyl, furyl, thiozolyl, imidazolyl, pyrazolyl, triazinyl, quinolyl or isoquinolyl.

5. The compound of claim 1 selected from the group consisting of: N-Benzyloxycarbonyl-L-aspartic acid 2-phenyltetronoyloxymethyl ketone, N-Benzyloxycarbonyl-L-aspartic acid 2-(3,4-dichlorophenyl)tetronoyloxymethyl ketone, N-Benzyloxycarbonyl-L-aspartic acid 2-benzyl-5,5-dimethyl tetronoyloxymethyl ketone, N-Benzyloxycarbonyl-L-aspartic acid tetronoyloxymethyl ketone and N-Benzyloxycarbonyl-L-aspartic acid 2-(4-methoxyphenyl) tetronoyloxymethyl ketone.

6. The compound of claim 1 selected from the group consisting of: N-Benzyloxycarbonyl-L-aspartic acid 2-benzyl tetronoyloxymethyl ketone, N-Benzyloxycarbonyl-L-valine-L-aspartic acid 2-phenyl tetronoyloxymethyl ketone, N-Benzyloxycarbonyl-L-aspartic acid 2-phenyl-5,5-dimethyl tetronoyloxymethyl ketone, N-Benzyloxycarbonyl-L-valine-L-aspartic acid 2-benzyl tetronoyloxymethyl ketone and N-Benzyloxycarbonyl-L-aspartic acid 5,5-dimethyl tetronoyloxymethyl ketone.

7. The compound of claim 1 selected from the group consisting of: N-Benzyloxycarbonyl-L-aspartic acid 2-chloro tetronoyloxymethyl ketone, N-Benzyloxycarbonyl-L-valineoL-alanine-L-aspartic acid 2-benzyl tetronoyloxymethyl ketone, N-Benzyloxycarbonyl-L-aspartic acid 2-methyl cyclopentadionoyloxy methyl ketone and N-Benzyloxycarbonyl-L-aspartic acid 2-phenylcyclopentadionoyloxymethyl ketone.

8. A pharmaceutical composition for inhibiting interleukin-1β protease comprising the formula (I) or a pharmaceutically acceptable salt thereof

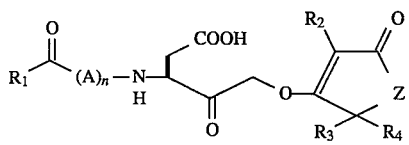

wherein $R_1$ is $(CR_5R_6)_n$, $(CR_5R_6)_n$-aryl, $(CR_5R_6)_n$-heteroaryl, $X-(CR_5R_6)_n$, $X-(CR_5R_6)_n$-aryl or $X-(CR_5R_6)_n$-heteroaryl wherein aryl and heteroaryl may be optionally substituted;

X is O or $NR_5$;

$R_5$ and $R_6$ are independently H or lower alkyl;

$R_2$ is H, halo, lower alkyl or $(CR_5R_6)_n$-aryl;

$R_3$ and $R_4$ are independently H or alkyl;

A is a D or L isomer of an andno acid selected from the group consisting of alaninc, valine, leucine, isoleucine, proline, phenylalanine, glycine, tyrosine, methionine, asparagine, glutamine, aspattic acid, glutamic acid, lysine, arginine, histidine and β-thienylalanine;

Z is $CH_2$ or O; and n is 0–4.

in a pharmaceutically acceptable carrier.

9. The pharmaceutical composition of claim 8 wherein said compound is selected from the group consisting of: N-Benzyloxycarbonyl-L-aspartic acid 2-phenyltetronoyloxymethyl ketone, N-Benzyloxycarbonyl-L-aspartic acid 2-(3,4-dichlorophenyl)tetronoyl-oxymethyl ketone, N-Benzyloxycarbonyl-L-aspartic acid 2-benzyl-5,5-dimethyltetronoyloxymethyl ketone, N-Benzyloxycarbonyl-L-aspartic acid tetronoyloxymethyl ketone and N-BenzyloxycarbonyloL-aspartic acid 2-( 4-methoxyphenyl) tetronoyloxymethyl ketone.

10. The pharmaceutical composition of claim 8 wherein said compound is selected from the group consisting of: N-Benzyloxycarbonyl-L-aspartic acid 2-benzyl tetronoyloxymethyl ketone, N-Benzyloxycarbonyl-L-valine-L-aspartic acid 2-phenyl tetronoyloxymethyl ketone, N-Benzyloxycarbonyl-L-aspartic acid 2-phenyl-5,5-dimethyl tetronoyloxymethyl ketone, N-Benzyloxycarbonyl-L-valine-L-aspartic acid 2-benzyl tetronoyloxymethyl ketone and N-Benzyloxycarbonyl-L-aspartic acid 5,5-dimethyl tetronoyloxymethyl ketone.

11. The pharmaceutical composition of claim 8 wherein said compound is selected from the group consisting of: N-Benzyloxycarbonyl-L-aspartic acid 2-chloro tetronoyloxymethyl ketone, N-Benzyloxycarbonyl-L-valine-L-alanine-L-aspartic acid 2-benzyl tetronoyloxymethyl ketone, N-Benzyloxycarbonyl-L-aspartic acid 2-methyl cyclopentadionoyloxy methyl ketone and N-Benzyloxycarbonyl-L-aspartic acid 2phenylcyclopentadionoyloxymethyl ketone.

12. A method of inhibiting interleukin-1β protease activity in a mammal in need of such treatment comprising administering to said mammal an effective inhibitory amount of a pharmaceutical composition comprising a compound of the formula (I) or a pharmaceutically acceptable salt thereof:

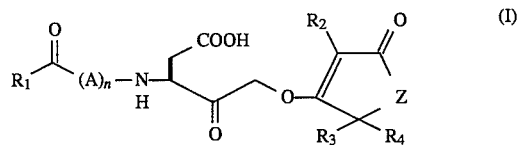

wherein $R_1$ is $(CR_5R_6)_n$, $(CR_5R_6)_n$-aryl, $(CR_5R_6)_n$-heteroaryl, $X-(CR_5R_6)_n$, $X-(CR_5R_6)_n$-aryl or $X-(CR_5R_6)_n$-heteroaryl wherein aryl and heteroaryl may be optionally substituted;

X is O or $NR_5$;

$R_5$ and $R_6$ are independently H or lower alkyl;

$R_2$ is H, halo, lower alkyl or $(CR_5R_6)_n$-aryl;

$R_3$ and $R_4$ are independently H or alkyl;

A is a D or L isomer of an amino acid selected from the group consisting of alanine, valine, leucine, isoleucine, proline, phenylalanine, glycine, tyrosine, methionine, asparagine, glutamine, aspartic acid, glutamic acid, lysine, arginine, histidine and β-thienylalanine;

Z is $CH_2$ or O; and n is 0–4.

in a pharmaceutically acceptable carrier.

13. The method of claim 12 wherein said compound is selected from the group consisting of: N-Benzyloxycarbonyl-L-aspartic acid 2-phenyltetronoyloxymethyl ketone, N-Benzyloxycarbonyl-L-aspartic acid 2-(3,4-dichlorophenyl)tetronoyloxymethyl ketone, N-Benzyloxycarbonyl-L-aspartic acid 2-benzyl-5,5-dimethyl tetronoyloxymethyl ketone, N-Benzyloxycarbonyl-L-aspartic acid tetronoyloxymethyl ketone and N-Benzyloxycarbonyl-L-aspartic acid 2-(4-methoxyphenyl) tetronoyloxymethyl ketone.

14. The method of claim 12 wherein said compound is selected from the group consisting of: N-Benzyloxycarbonyl-L-aspartic acid 2-benzyl tetronoyloxymethyl ketone, N-Benzyloxycarbonyl-L-valine-L-aspartic acid 2-phenyl tetronoyloxymethyl ketone, N-Benzyloxycarbonyl-L-aspartic acid 2-phenyl-5,5-dimethyl tetronoyloxymethyl ketone, N-Benzyloxycarbonyl-L-valine-L-aspartic acid 2-benzyl tetronoyloxymethyl ketone and N-Benzyloxycarbonyl-L-aspartic acid 5,5-dimethyl tetronoyloxymethyl ketone.

15. The method of claim 12 wherein said compound is selected from the group consisting of: N-Benzyloxycarbonyl-L-aspartic acid 2-chloro tetronoyloxymethyl ketone, N-Benzyloxycarbonyl-L-valine-L-alanine-L-aspartic acid 2-benzyl tetronoyloxymethyl ketone, N-Benzyloxycarbonyl-L-aspartic acid 2-methyl cyclopentadionoyloxy methyl ketone and N-Benzyloxycarbonyl-L-aspartic acid 2-phenyl-cyclopentadionoyloxymethyl ketone.

* * * * *